United States Patent
Furuyashiki et al.

(10) Patent No.: US 8,461,130 B2
(45) Date of Patent: Jun. 11, 2013

(54) FOOD CONTAINING GLYCOGEN AND USE THEREOF

(75) Inventors: Takashi Furuyashiki, Amagasaki (JP); Hiroki Takata, Kobe (JP); Hideki Kajiura, Amagasaki (JP)

(73) Assignee: Ezaki Glico Co., Ltd., Osaka (JP)

( * ) Notice: Subject to any disclaimer, the term of this patent is extended or adjusted under 35 U.S.C. 154(b) by 710 days.

(21) Appl. No.: 12/448,591

(22) PCT Filed: Dec. 26, 2007

(86) PCT No.: PCT/JP2007/075012
§ 371 (c)(1),
(2), (4) Date: Oct. 16, 2009

(87) PCT Pub. No.: WO2008/081834
PCT Pub. Date: Jul. 10, 2008

(65) Prior Publication Data
US 2010/0063000 A1  Mar. 11, 2010

(30) Foreign Application Priority Data

Dec. 28, 2006 (JP) .................................. 2006-355124

(51) Int. Cl.
*A61K 31/715* (2006.01)
*A01N 43/04* (2006.01)

(52) U.S. Cl.
CPC .................................... *A61K 31/715* (2013.01)
USPC .......................................................... 514/54

(58) Field of Classification Search
None
See application file for complete search history.

(56) References Cited

U.S. PATENT DOCUMENTS

| 6,617,356 B2 * | 9/2003 | Goodman et al. ............ 514/565 |
| 7,229,801 B2 * | 6/2007 | Fujii et al. ..................... 435/101 |
| 7,670,812 B2 * | 3/2010 | Kajiura et al. ................ 435/101 |

FOREIGN PATENT DOCUMENTS

| JP | 2005-213185 | 8/2005 |
| WO | WO 97/29763 A1 * | 8/1997 |
| WO | 2006/035848 | 4/2006 |

OTHER PUBLICATIONS

M. J. O'Neil et al. (eds.), "The Merck Index, 13th Edition," Merck & Co., Whitehouse Station, NJ, 2001, only p. 801 supplied (see "Glycogen").*
International Search Report dated Apr. 1, 2008 in the International (PCT) Application PCT/JP2007/075012.
Kazuo Ryoyama et al., "Anti-Tumor Activity of an Enzymatically Synthesized α-1,6 Branched α-1,4-Glucan, Glycogen", Biosci. Biotechnol. Biochem., vol. 68, No. 11, pp. 2332-2340, 2004.
Kajiura et al., "Nihon Ouyou Toushitu Kagakukai Taikai Kouen Youshisyu", The Japanese Society of Applied Glycoscience, lecture summaries of 2006, J. Appl. Glycosci., 53, Suppl., p. 27, 2006.
Takata et al., "Nihon Ouyou Toushitu Kagakukai Taikai Kouen Youshisyu", The Japanese Society of Applied Glycoscience, lecture summaries of 2006, J. Appl. Glycosci., 53, Suppl., p. 27, 2006.
Gary L. Brammer et al., "Distribution of α-Amylase-Resistant Regions in the Glycogen Molecule", Carbohydrate Research, vol. 24, pp. 343-354, 1972.

* cited by examiner

*Primary Examiner* — Lawrence E Crane
(74) *Attorney, Agent, or Firm* — Wenderoth, Lind & Ponack, L.L.P.

(57) ABSTRACT

The present invention is directed towards improving blood glucose levels, visceral fat levels, blood cholesterol levels, neutral fat levels, etc. by oral administration of enzyme synthesized glycogen (ESG). The invention is further directed towards the intake of food by a subject that comprises ESG as a carbohydrate to improve blood glucose levels, visceral fat levels, blood cholesterol levels, neutral fat levels and the like.

12 Claims, 4 Drawing Sheets

FOOD CONTAINING GLYCOGEN AND USE THEREOF

This application is a 371 U.S. national stage of International Application No. PCT/W2007/075012 filed Dec. 26, 2007, herein incorporated by reference in its entirety.

TECHNICAL FIELD

The present invention relates to a glycogen-containing food and glycogen-containing orally-administered formulation. Compared to other saccharides such as sugar, starch, and dextrin, glycogen provides a modest increase in the blood glucose level and slight insulin secretion, and therefore is suitably used in dietary therapy for individuals having high blood glucose levels, prediabetes, and mild diabetes.

Glycogen possesses several useful effects such as intestine-regulating effects associated with improved intestinal flora achieved by an increase in *Lactobacillus* and *Bifidobacterium* in human and animal intestines and improved bowel movement achieved by an increase in fecal moisture, an increase in good cholesterol (HDL), a decrease in bad cholesterol (LDL), a decrease in total cholesterol, a reduction in neutral fat, and a reduction in body fat; and it is effective for preventing or improving lifestyle-related diseases (e.g., obesity, arteriosclerosis, cardiopathy, and diabetes) and metabolic syndrome. Such useful effects of glycogen are applicable not only to human beings but also to livestock and pets. The present invention also relates to a food and supplement for livestock and pets.

BACKGROUND ART

Glycogen, known as a storage polysaccharide in animals, is a highly-branched polymer in which a large amount of glucose is linked by α-1,4 glycosidic linkages. Glycogen is made primarily in the liver and skeletal muscles and functions as a transient storage medium for excess glucose.

Glycogen synthesis and breakdown is regulated by tyroxine, glucagon, insulin, adrenalin, etc., which are secreted depending on the physiological state, e.g., blood glucose level.

Although glycogen-containing compositions are known (Patent Document 1), almost no studies are conducted on their role other than those of energy storage and immune system activation (Non-Patent Document 1).

Glycogen can be obtained from animals (e.g., oysters) or plants; however, synthesized products are also known and their anticancer effects are studied (Non-Patent Document 1). Patent Document 2 discloses a production process of glycogen.

Patent Document 1:
Japanese Unexamined Patent Publication No. 2000-007707
Patent Document 2:
WO2006/035848
Non-Patent Document 1:
Ryoyama, K.; Kidachi, Y.; Yamaguchi, H.; Kajiura, H.; Takata, H. (2004) Biosci Biotechnol Biochem 68, 2332-2340

DISCLOSURE OF THE INVENTION

Problems to be Solved by the Invention

Excessive calorie intake problematically leads to obesity, in particular, metabolic syndrome (a combination of disorders including increased body fat (e.g., visceral fat), hyperglycemia, hypercholesterolemia, and hyperlipidemia), which further results in arteriosclerosis, diabetes, and like lifestyle-related diseases. However, limiting caloric intake to prevent obesity is difficult, and dietary control does not last long without essential nutrient intake. Further, the intestine plays an important role for immune systems or the like when contacted with a foreign substance in food; increasing useful bacteria such as *Bifidobacterium* and *Lactobacillus* to improve the balance of enteric bacteria is necessary not only for the prevention of life style-related diseases but for the maintenance of good health.

Means for Solving the Problems

In view of the aforementioned problems, the present inventors conducted further studies and found that glycogen produces the following useful effects in addition to energy storage and immune activation effects: a decrease in the blood glucose level, reduction of insulin production/secretion, improvement of the intestinal environment especially the intestinal flora, stimulation of bowel movement, reduction of body fat especially visceral fat, increase in the proportion of HDL cholesterol (known as good cholesterol), decrease in bad (LDL) cholesterol, decrease in blood cholesterol, and a decrease in neutral fat in blood. The present invention was thus accomplished.

The effects of the present glycogen are particularly seen in human beings; however, they are also effective for livestock (cows, pigs, hens, horses, etc.) and pets (dogs, cats, etc.).

The object of the present invention is to provide the following inventions.

1. A low insulin food containing glycogen.
2. Use of glycogen for suppressing a blood glucose level increase and insulin secretion level per unit calorie intake.
3. A food for reducing body fat/visceral fat, the food containing glycogen.
4. Use of glycogen for reducing the proportion of body fat, particularly, visceral fat relative to body weight.
5. A diet food containing glycogen.
6. Use of glycogen for suppressing body weight increase.
7. A food for intestinal regulation, the food containing glycogen.
8. Use of glycogen for regulating gastrointestinal conditions.
9. A *Bifidobacterium* growth promotant containing glycogen.
10. Use of glycogen for promoting *Bifidobacterium* growth.
11. Use of glycogen for increasing the proportion of *Bifidobacteria* among enteric bacteria.
12. A *Lactobacillus* growth promotant containing glycogen.
13. Use of glycogen for promoting *Lactobacillus* growth.
14. Use of glycogen for increasing the proportion of *Lactobacillus* among enteric bacteria.
15. A food for reducing neutral fat, the food containing glycogen.
16. Use of glycogen for reducing the blood neutral fat level.
17. A food for reducing the total blood cholesterol level, the food containing glycogen.
18. Use of glycogen for reducing the total blood cholesterol level.
19. A food for increasing the proportion of HDL cholesterol relative to the total cholesterol, the food containing glycogen.
20. Use of glycogen for increasing the proportion of HDL cholesterol of the total blood cholesterol.
21. An orally-administered formulation containing glycogen.
22. The formulation according to Item 21, which is in the form of food comprising an obvious food and/or supplement.
23. A food for pets and livestock, the food containing glycogen.

24. A food for reducing liver fat, the food containing glycogen.

25. A food for suppressing absorption of fat, the food containing glycogen.

26. A food, use, or formulation according to any one of Items 1 to 25, wherein the glycogen is included or used as a highly purified extract.

Effects of the Invention

Glycogen performs a role of storing energy in the muscles and liver in vivo. Oral or parenteral (particularly transdermal) administration of glycogen leads to, while providing calories essential for life and health maintenance, a reduction in blood glucose level, insulin secretion, body fat (particulary visceral fat), total blood cholesterol, LDL (bad) cholesterol, neutral fat, etc., and an increase in the proportion of good HDL cholesterol, thus preventing lifestyle-related diseases including circulatory system diseases attributable to diabetes and arteriosclerosis. Further, improvement of the absolute number and proportion of useful bacteria (e.g., *Lactobacillus* and *Bifidobacterium*) results in improved intestinal flora. In addition, an increase in fecal moisture promotes bowel movement and provides relief from constipation or hemorrhoids. Furthermore, it is also effective for reducing liver fat and suppressing the absorption of fat.

Since glycogen has such excellent effects, intake of glycogen as food (including foods for livestock and pets as well as foods for human beings) or drugs (including veterinary drugs) can prevent lifestyle-related diseases and metabolic syndrome, or delay the onset of these diseases in individuals who have a high risk of contracting these diseases.

The glycogen used in the present invention is a safe material having no side effects.

Long-term intake of the glycogen used in the present invention results in a modest rise, followed by a persistent reduction in postprandial blood glucose level and insulin secretion, allowing for a reduction of the blood glucose level and insulin level without causing a risk of hypoglycemia. Therefore, it is safe for subjects having normal or high blood glucose levels, or subjects who are prediabetic. Further, even when the intake of glycogen is discontinued, the postprandial blood glucose level, insulin secretion level, reduction of body fat (particularly visceral fat), reduction in the blood cholesterol level, increase in the proportion of HDL cholesterol, improvement of the intestinal flora, etc., gradually return to their previous state before glycogen intake without rebound.

The glycogen of the present invention is suitably administered to a healthy person or patient having risk factors (hereditary or environmental factors) for obesity (particularly visceral obesity) associated with circulatory system diseases including hyperglycemia, diabetes, intestinal diseases, and arteriosclerosis.

BEST MODE FOR CARRYING OUT THE INVENTION

Figure 1:
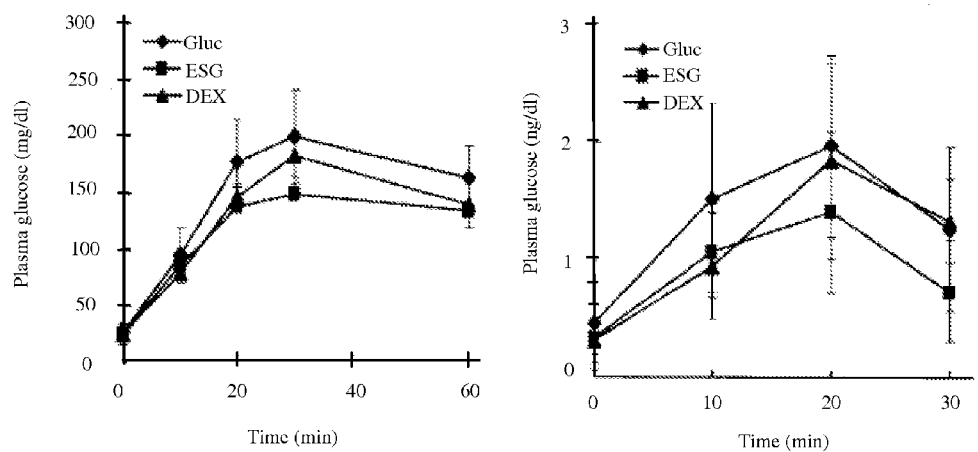
FIG. 1 discloses graphs showing changes in blood glucose level and insulin level when glycogen was administered.

The glycogen used in the present invention is known to be stored in animal livers and skeletal muscles, and is generally derived from animals. However, it is known that plants and microorganisms produce glycogen or a material having the same structure as glycogen (for example, WO2006/035848), and these are all usable as the glycogen of the present invention. Glycogen can be synthesized using enzyme. For example, a method of using sucrose phosphorylase (EC 2.4.1.7) and α-glucan phosphorylase (EC 2.4.1.1) with sucrose (Non-Patent Document 1), and a method of using branching enzyme (EC 2.4.1.18) with short-chain amylose (Patent Document 2 and Non-Patent Document 2) are known. Glycogen synthesized using such methods is known to have a similar chemical structure and physical structure to those of natural glycogens (Non-Patent Documents 2 and 3), and such enzymatically synthesized glycogen can be utilized as the glycogen of the present invention. The glycogen preferably has a molecular weight of about $1 \times 10^6$ to about $2 \times 10^7$, but those having a higher molecular weight or lower molecular weight can be widely used.

Non-Patent Document 2: Kajiura, Takata, Akiyama, Takeda, and Kuriki (2006), *Nihon Ouyou Toushitu Kagakukai Taikai Kouen Youshisyu* 2006, The Japanese Society of Applied Glycoscience, lecture summaries of 2006: J. Appl. Glycosci., 53, Suppl., p 27

Non-Patent Document 3: Takata, Kajiura, Kuriki, and Kitamura (2006), *Nihon Ouyou Toushitu Kagakukai Taikai Kouen Youshisyu* 2006, The Japanese Society of Applied Glycoscience, lecture summaries of 2006: J. Appl. Glycosci., 53, Suppl., p 27

It is preferable to use enzymatically synthesized glycogen (ESG) as the glycogen of the present invention. Preferable examples thereof include those with a molecular weight in the hundreds of thousands to several million after being digested by α-amylase. A theoretical limitation is not desired; however, the present inventors guess that the enzymatially synthesized glycogen digested by α-amylase has a high molecular weight for the following reason. Specifically, glycogen has a spherical molecular structure, and α-amylase digests glycogen by cleaving α-1,4-glycosidic linkages from the periphery of the glycogen molecule. However, especially in ESG, the density of the branching structure (branching by α-1,6-glycoside bonds) increases as the molecular entrails become closer. When the density of the branching structure is above a certain level, α-amylase cannot digest glycogen. In the case of ESG, when the branching density of glycogen is improved in a degree such that α-amylase digestion does not occur, the molecular weight of glycogen is in the hundreds of thousands to several million. Accordingly, a molecule having such a molecular weight is maintained. On the other hand, most natural glycogens, for example, mussel (blue mussel)-derived glycogen, are digested by α-amylase to fragments having an extremely small molecular weight. This is presumably because most natural glycogens include both a high branching density portion and a low branching density portion (i.e., having a non-uniform branching density), and relatively long straight chain portions of α-1,4-glycosidic linkages are present in the molecule. This structure is also shown in Non-Patent Document 4.

Non-Patent Document 4: Brammer, G. L.; Rougvie, M. A; French, D. (1972) Carbohydr. Res. 24, 343-354

Non-Patent Document 4 discusses that natural glycogen has a non-uniform branching density due to repeated intracellular synthesis and degradation.

However, some natural glycogens have a molecular weight in the hundreds of thousands to several million after α-amylase digestion, and thus are preferable. This is presumably because glycogen having a uniform branching density can be synthesized, even if it is in nature, depending on physiological conditions. For example, limpet-derived glycogen is preferable since it has a molecular weight in the hundreds of thousands to several million after α-amylase digestion.

More specifically, glycogen having a uniform branching density, such as enzymatically synthesized glycogen or limpet-derived glycogen, that retains at least 5% (e.g., 5 to 40%) of its original molecular weight after α-amylase breakdown for 3 to 24 hours, or glycogen having a resistant starch (RS) content of about 15 to about 25% when reacting with pancreatin and glucoamylase is preferably used.

The glycogen of the present invention can be used per se as food, or can be used singly or in a combination with an appropriate atoxic orally-administered carrier, diluent, or excipient, to make food formulations or medical formulations such as tablets (uncoated tablets, sugar-coated tablets, effervescent tablets, film-coated tablets, chewable tablets, etc.), capsules, troches, powders, subtle granules, granules, solutions, suspensions, emulsions, pastes, creams and sustained-release formulations (e.g., enteric tablets, capsules, or granules). The amount of the glycogen in the formulation can be suitably determined, but is typically in the range of 0.01 to 100 wt %.

In the present invention, some or all of the saccharides in food are replaced by glycogen, resulting in a reduction in blood glucose level, insulin secretion, body fat (particularly visceral fat), total blood cholesterol, LDL (bad) cholesterol, neutral fat, etc., and an increase in the proportion of good HDL cholesterol, while providing essential calories.

(In particular, visceral fat), the total blood cholesterol, LDL (bad) cholesterol, neutral fat, etc. can be reduced, and the proportion of good HDL cholesterol can be increased.

The glycogen used in the present invention can be added as a saccharide to known foods.

Examples of foods to which glycogen is added or mixed include drinks (soft drinks (coffee, cocoa, juice, mineral drinks, tea drinks (green tea, tea, oolong tea) etc.), milk beverages, lactic acid bacteria beverages, yogurt beverages, carbonated beverages, alcoholic drinks); spreads (custard cream, butter cream, peanut cream, chocolate cream, cheese cream, etc.); pastes (fruit pastes, vegetable pastes, sesame pastes, seaweed pastes, etc.); western-style sweets (chocolates, doughnuts, pies, muffins, waffles, gums, gummy candies, jellies, candies, cookies, crackers, biscuits, snacks, cakes, puddings, etc.); Japanese sweets (ame (candies), sembei (rice crackers), karinto (bite-sized or short cylinder-shaped rice crakers), arare (small rice crackers), dango (Japanese dumplings made from mochiko (rice flour)), ohagi (rice cake with sweet beans), daifuku (soft rice cake with azuki bean jam), mame-mochi (rice cake with beans), mochi (rice cakes), an (bean paste jam), manju (steamed azuki bean jam-filled bun), kasutera (sponge cakes), anmitsu (gelatin mixed with an and other ingredients), youkan (azuki bean jelly), etc.); frozen desserts (ice cream, ice candies, sherbets, etc.); retort pouched foods (curry, stew, gyu-don (beef and onion stew on a bowl of rice), chuka-don (pork and vegetable stew on a bowl of rice), zousui (risotto), okayu (rice porridge), miso soup, soup, meat sauce, demiglace sauce, meatball, hamburger, oden (fish cake stew), sekihan (rice boiled with red beans), yakitori, chawan-mushi (steamed egg custard), etc.); instant foods (instant ramen (noodles), instant harusame (instant bean-jelly noodles) soup, instant yuba (instant soybean curd film) noodle soup, instant udon (wheat noodles), instant soba (buckwheat noodles), instant yakisoba (fried noodles), instant spaghetti, instant won ton noodles, instant siruko (sweet azuki bean soup), miso soup mix, powdered soup mix, powdered juice mix, pancake mix, etc.); bottled/canned foods, jelly like foods (jelly, agar, jelly like drink, etc.); seasonings (soy sauce, mirin (sweet sake), vinegar, miso, dressing, chemical seasoning, complex seasoning, sauce, mayonnaise, ketchup, furikake (seasoned fish meal), tentsuyu (sauce for Japanese deep-fat fried food), mentsuyu (noodle soup), dashi-no-moto (instant stock mix), chuka-soup-no-moto (instant mix for Chinese soup), bouillon, yakiniku-no-tare (sauce for Japanese grilled meat), reishabu-no-tare (sauce for a cold version of shabu shabu), curry roux, stew roux, etc.); milk products (milk, cheese, yogurt, butter, whipped cream, etc.); processed fruits (jam, marmalade, fruits preserved in syrup, dry fruits, etc.); processed grain foods (noodles, pasta, bread, rice noodles, etc.); Japanese pickles (takuan (pickled radishes), nara-zuke (pickles seasoned with sake lees), kimchee, fukujin-zuke (sliced vegetables pickled in soy sauce and dyed red), rakkyou-zuke (pickled shallots), hakusai-zuke (pickled cabbages), karashi-zuke (pickles seasoned with mustard sauce), shiba-zuke (assorted vegetables hashed and pickled in salt), asa-zuke (fresh vegetables preserved with salt or malt), pickles, etc.); tukemono-no-moto (premix for pickles) (premix for instant pickles, premix for kimchee, etc.); fish meat products (kamaboko (boiled fish paste), chikuwa (tabular fish cakes), hanpen (cake of pounded fish), etc.); processed meats (ham, sausage, salami, bacon, etc.); chinmi (relish) (sakisurume (dried squid strips), sakitara (dried cod) uni-no-shiokara (salted guts of sea urchin), ika-no-shiokara (salted guts of squid), tako-no-shiokara (salted guts of octopus), kawahagi-no-mirin-boshi (dried mirin-seasoned filefish), fugu-no-mirin-boshi (dried mirin-seasoned swellfish), ika-no-kunsei (sliced smoked squid), konowata-no-shiozuke (salted and fermented trepang guts), etc.); dried foods (seasoned layer etc.); daily dishes (dressed foods, fried foods, pan-fried foods, baked foods, simmered foods, vinegared foods, etc.); frozen foods (fried shrimp, croquette, egg roll, pork cutlet, shao mai, jiao-zi, tako-yaki (ball of fried batter containing a diced pieces of octopus), nikuman (steamed bun with cooked pork or other ingredients), anman (steamed bun with azuki beans), etc.).

Foods to which the glycogen of the present invention is added or mixed may be so-called health foods, functional foods, nutritional supplements, supplements, Foods For Specified Health Use, Medical Foods for the Ill/several foods-containing Medical Foods for the Ill (Ministry of Health, Labor and Welfare, one of the Foods for Special Dietary Use), and Foods for the Elderly (Ministry of Health, Labor and Welfare, one of the Foods for Special Dietary Use). In this case, foods may be in the form of uncoated tablets, film-coated tablets, sugar-coated tablets, granules, powders, tablets, capsules (containing both hard and soft capsules), chewable forms, syrups, drinks, etc. The foods to which the glycogen of the present invention is added or mixed can be prepared using a per-se known method.

Foods containing the glycogen of the present invention (e.g., Foods For Specified Health Use) are particularly effective for those who have high normal blood glucose levels, those who are anxious about their blood glucose levels, including prediabetic (for slowing a rise in the postprandial blood glucose levels), those who are worried about their cholesterol levels, those who have high (high normal) blood pressures due to arteriosclerosis or who have mild hypertension, those who want to regulate their stomach conditions, those who are concerned about neutral fat, those who are concerned about visceral obesity, etc.

The glycogen of the present invention has a variety of effects on the metabolism in vivo, such as suppressing the rise in the postprandial blood glucose level, slowing the rise in the serum insulin level, reducing neutral fat, reducing total cholesterol, increasing the proportion of HDL cholesterol, reducing visceral fat, etc., when absorbed directly from the lining of the mouth or gastrointestinal tract by way of oral administration, or when absorbed after partial hydrolyzation in the gastrointestinal tract. Therefore, continuous intake of the glycogen is possible and preferable to prevent diabetes, arteriosclerosis, visceral obesity and associated circulatory system diseases, and to alleviate and regulate such tendencies. The glycogen of the present invention is preferably used as functional foods, especially as Foods for Specified Health Use, for preventing the aforementioned diseases. When the present glycogen or formulation is used for the above purpose, it may be orally administered to an adult weighting 60 kg in an amount of 0.1 g to 100 g per day, preferably 1 to 100 g per day, and more preferably 10 to 100 g per day.

EXAMPLES

The present invention will be described in greater detail below, using the Examples.

Example 1

Glucose (Gluc), glycogen (ESG), and dextrin (DEX) were each orally administered to Sprague Dawley (SD) rats (male, 6 weeks old) in a dose of 2 g/kg body weight (7 rats per group) after fasting for 16 hours. Blood was collected via the tail vein before and 10, 20, 30, and 60 minutes after the administration, and the collected blood was centrifuged to obtain blood plasma samples. The glucose content in each blood plasma sample was measured using Glucose CII-Test Wako, and the insulin level was measured using a rat insulin ELISA kit (Shibayagi, Gunma, Japan). The results are shown in FIG. 1. The results of FIG. 1 show that the blood glucose level and insulin secretion of the glycogen-fed group were low after the administration, and the blood glucose level and insulin secretion gradually increased after feeding. This has revealed that glycogen can prevent or slow the progression of diabetes in mammalians, e.g., humans, that have a reduced insulin secretion capacity or insulin resistance. Note that ESG denotes enzymatically synthesized glycogen.

Example 2

SD rats (male, 6 weeks old) were fed one of the diets with the compositions shown in Table 1 for 2 weeks, and body weight was measured once in 2 to 3 days during the feeding period. Table 2 below shows changes in body weight and food intake.

The results of Table 2 below show that, although a tendency for the glycogen-fed group to have a slightly lower food intake and body weight was observed, the difference was not significant, revealing that glycogen has no effect on the growth or feeding behavior of animals. This has also established the safety of glycogen.

TABLE 1

Diet Composition

| | Diet Group | | |
|---|---|---|---|
| | CS | ESG | ESG25% |
| α-CS | 63 | — | 47.25 |
| ESG | — | 63 | 15.75 |
| Casein | 20 | 20 | 20 |
| Cellulose | 5 | 5 | 5 |
| Corn Oil | 5 | 5 | 5 |
| Mineral Mix | 5 | 5 | 5 |
| Vitamin Mix | 2 | 2 | 2 |

α-CS: pregelatinized corn starch
ESG: enzymatically synthesized glycogen
The mineral mix and vitamin mix used were blended by Oriental Yeast Co., ltd . . .

TABLE 2

Changes in Body Weight and Food Intake of Rats

| | Diet Group | |
|---|---|---|
| | CS | ESG |
| Initial Body Weight | 199 ± 7 | 198 ± 6 |
| Final Body Weight | 294 ± 13 | 283 ± 14 |
| Food Intake | 23.6 ± 1.5 | 22.3 ± 0.8 |

Measured once in 2-3 days during the feeding period.

Example 3

SD rats (male, six weeks old) were fed one of the diets with the compositions shown in Table 1 for 2 weeks, and feces were collected on the 10th and 11th days of feeding, after which the feces were freeze-dried and the dry weight was measured.

The moisture content was determined by collecting fresh feces from the anus on the 10th to 11th day of feeding, and weighing the feces before and after freeze-drying. Table 3 below shows the dry weight, the moisture content, and the wet weight of the feces.

The results of Table 3 below reveal that, although glycogen (ESG) did not vary from corn starch (CS) in terms of the dry weight of feces, glycogen (ESG) increased the moisture content, which increased the wet weight of feces on the whole. It is believed that the decreased transit time of feces in the intestine improved the bowel movement, resulting in an increased moisture content of the feces.

These results have revealed that glycogen improves the bowel movement, and thus is useful for constipation, hemorrhoids, etc.

TABLE 3

Weights and Moisture Content of Rat Feces

| | Diet Group | |
|---|---|---|
| Feces | CS | ESG |
| Dry Weight (g/day) | 3.21 ± 0.49 | 2.78 ± 0.44 |
| Moisture Content (%) | 55.1 ± 9.3 | 68.0 ± 7.4* |
| Wet Weight (g/day) | 7.15 ± 1.09 | 8.69 ± 1.39* |

The wet weight was calculated from the dry weight and moisture content.
The data represent mean ± S.D. n = 7

Example 4

Figure 2:
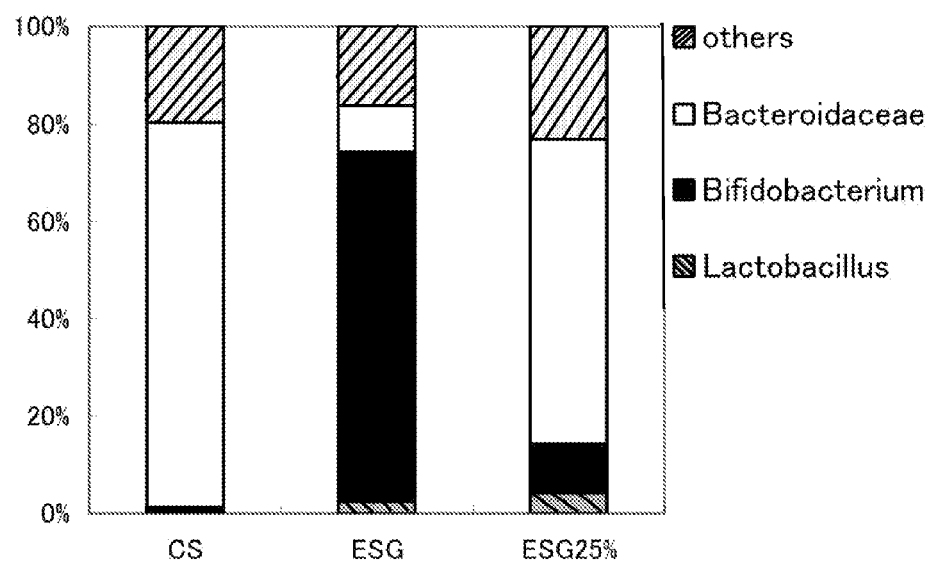
FIG. 2 is a bar chart showing proportions of intestinal bacteria.

SD rats (male, six weeks old) were fed one of the diets with the compositions shown in Table 1 for 2 weeks, fresh feces were collected from the anus on the 9th and 10th days of feeding, and the enteric bacterial count was determined by a culture method using the media shown in Table 4. The results are shown in Table 5 and FIG. 2. The results of Table 5 and FIG. 2 have revealed that glycogen (ESG) promotes the propagation of *Lactobacillus* and *Bifidobacterium*, which are useful enteric bacteria, and in particular, *Bifidobacterium*, to increase the proportion of these bacteria, thereby significantly improving the intestinal flora.

TABLE 4

Culture Media for Intestinal Bacteria

| Medium Name | Control Bacteria Group |
|---|---|
| For Aerobic Bacteria | |
| Trypticase Soy Blood Agar (base, BBL) | Aerobic Bacteria (Non-selective) |
| DHL Agar Medium (Eiken) | Enterobacteriaceae |
| TATAC Agar Medium | Streptococcus |
| PEES Agar Medium (base, Eiken, Staphylococcus 110) | Staphylococcus |
| Modified LBS Agar Medium (base, BBL) | Lactobacillus |
| For Anaerobic Bacteria | |
| BL Agar Medium (Nissui) | Anaerobic Bacteria (Non-selective) |
| BS Agar Medium (base, Nissui, BL Agar Medium) | Bifidobacterium |
| NBGT Agar Medium (base, Nissui, GAM Medium) | Bacteroidaceae |

For the media compositions, see Tomotari MITSUOKA, "Chonaikinno sekai (the World of Intestinal Bacteria)", 1984, Sobunsha.

TABLE 5

Effect of Glycogen on Intestinal Bacterial Count

| | Diet Group | | |
|---|---|---|---|
| | CS | ESG | ESG25% |
| | | $\log_{10}$ | |
| Bifidobacterium | 7.1 ± 0.66 | 10.7 ± 0.25** | 7.8 ± 1.30 |
| Bacteroidaceae | 9.5 ± 0.48 | 9.7 ± 0.52 | 9.5 ± 0.21 |
| Enterobacteriaceae | 6.8 ± 0.66 | 6.4 ± 0.43 | 6.4 ± 0.43 |
| Streptococcus | 7.4 ± 0.71 | 6.7 ± 0.57 | 7.1 ± 0.45 |
| Staphylococcus | 6.0 ± 0.44 | 4.4 ± 0.92 | 5.9 ± 0.60 |
| Lactobacillus | 7.6 ± 0.43 | 9.1 ± 0.45* | 8.4 ± 0.43* |

The data represent mean ± S.D. n = 7
The asterisks (*) () denote significant differences. (P < 0.01, *P < 0.05) vs. CS group

Example 5

SD rats (male, six weeks old) were fed one of the diets with the compositions shown in Table 1 for 2 weeks and then sacrificed, and the cecal contents were collected and measured for weight and pH.

Five volumes of water were added to the cecal contents and stirred well, after which the mixture was adjusted to a pH of 2.0 with $2MH_2SO_4$. The mixture was diluted with water to 10 times the original cecal contents, and subjected to centrifugal filtration (cut-off: 5 kDa) to obtain the filtrates as samples. The contents of short chain fatty acids (acetic acid, propionic acid, and butyric acid) in each sample were quantified by gas chromatography (Shimazu Corporation). Gas chromatography was performed under the following conditions: column: a Thermon-3000 packed column; vaporizing chamber temperature: 250° C.; column temperature: 130° C.; detector: FID at 250° C.; carrier gas: $N_2$ at 40 ml/min. The results are shown in Table 6 and FIG. 3.

Figure 3:
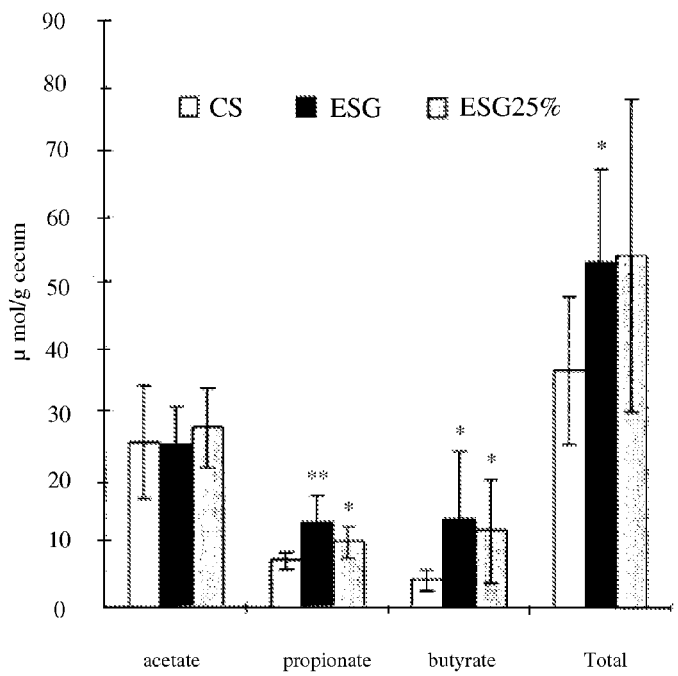
FIG. 3 is a bar chart showing changes in the contents of short-chain fatty acids in the cecums.

As is clear from the results of Table 6 and FIG. 3, glycogen (ESG) increased the wet weight of the cecal contents, and increased the production of short chain fatty acids (propionic acid and butyric acid), thus lowering the pH in the cecum. It is known that butyric acid and propionic acid have strong antibacterial properties, and are effective in the prevention of infections with pathogens such as enteropathogenic *E. coli, Salmonella, Shigella*, etc., and also act on the immune system to inhibit enteritis such as ulcerative colitis. Therefore, the intake of glycogen proved to balance the intestinal environment, and effectively serve to inhibit intestinal diseases.

TABLE 6

Effects on the Weight and pH of the Cecal Contents of Rats

| | Diet Group | | |
|---|---|---|---|
| Cecal Contents | CS | ESG | ESG25% |
| Wet Weight (g) | 2.01 ± 0.45 | 5.52 ± 1.30** | 2.55 ± 0.26* |
| pH | 8.14 ± 0.27 | 7.27 ± 0.28** | 7.61 ± 0.19** |

The wet weight was calculated from the dry weight and moisture content.
The data represent mean ± S.D. n = 7
The asterisks (*) (**) denote significant differences. (*P < 0.05, **<0.01) vs. CS group

Example 6

SD rats (male, six weeks old) were fed one of the diets with the compositions shown in Table 1 for 2 weeks and then sacrificed, after which blood was collected from the hearts and centrifuged to obtain blood plasma samples. The neutral fats, cholesterol, and HDL-cholesterol in each sample were measured respectively using Triglyceride E-Test Wako, Cholesterol-E-Test Wako, and HDL-Cholesterol Test Wako. Further, the liver and the fat around the testis in each sacrificed rat were weighed.

The results are shown in Tables 7 and 8.

TABLE 7

Effect of Reducing Body Fat (Around the Testis); the Liver as Control

| | Diet Group | |
|---|---|---|
| Weight | CS | ESG |
| Liver | 11.9 ± 1.3 | 11.7 ± 1.2 |
| Epididymal Fat | 4.17 ± 0.88 | 3.27 ± 0.61* |

The data represent mean ± S.D. n = 7
The asterisk (*) denotes a significant difference (P < 0.05) vs. CS group

TABLE 8

Effect of Reducing the Blood Lipids in Rats

| | Diet Group | |
|---|---|---|
| | CS | ESG |
| Triglycerides (mg/dl) | 135 ± 32 | 82 ± 30** |
| Cholesterol Total (mg/dl) | 62.2 ± 5.5 | 47.2 ± 4.2** |

TABLE 8-continued

Effect of Reducing the Blood Lipids in Rats

| | Diet Group | |
|---|---|---|
| | CS | ESG |
| HDL- (mg/dl) | 42.1 ± 3.1 | 34.2 ± 3.3* |
| HDL/Total (%) | 67.8 ± 3.0 | 72.5 ± 2.8* |

The data represent mean ± S.D.
The asterisks (*) (**) denote significant differences (*P < 0.05, **<0.01) vs. CS group The results of Table 7 have revealed that glycogen (ESG) reduces the body fat compared to corn starch (CS). The body fat around the testis is an example of visceral fat; thus, glycogen proved to be particularly effective in reducing the visceral fat. Visceral fat is one primary cause for metabolic syndrome and lifestyle-related diseases. Thus, glycogen proved to be capable of preventing or treating metabolic syndrome and lifestyle-related diseases, or slowing the progression or inhibiting the aggravation of such diseases.

Further, as shown in Table 8, glycogen can reduce the neutral fats and the total blood cholesterol level, and can also increase the proportion of HDL cholesterol, which is known as good cholesterol. Both neutral fats and cholesterol are deeply involved in arteriosclerosis and associated cerebrovascular diseases (cerebral apoplexy, myocardial infarction, angina pectoris, etc.). Thus, glycogen proved to be capable of preventing or treating these diseases, or slowing the progression or inhibiting the aggravation of these diseases.

Test Example 1

Glycogen Evaluation Methods

Method 1

Glycogen was evaluated using the Resistant Starch Assay Kit; Megazyme International Ireland Ltd. (Wicklow, Ireland), based on the content of the "resistant starch (RS)" quantified according to the manual. This method is employed as an official method for measuring the RS content (AOAC Method 2002.02; AACC Method 32-40). Specifically, the RS content was determined according to the following scheme.

Scheme

Digest 100 mg of a sample in an enzyme solution (1% pancreatin + 12 U glucoamylase)

↓ 37° C., 16 hr

Add an equal volume of ethanol to the reaction product, followed by centrifugation at low speed (1500 × g, 10 min)

↓ → Quantify the glucose in the supernatant
→ Resistant starch content

Solubilize the pellet with an alkali

↓

Immediately after neutralization, digest the resulting product by a large quantity of glucoamylase (330 U) (50° C., 30 min)

↓ → Quantify the gluclose
→ Resistant starch content

The results are shown in Table 9.

TABLE 9

| | Name | RS Content (%) |
|---|---|---|
| Enzymatically Synthesized | 8000 kDa | 22.0 ± 1.4 |
| | 3000 kDa | 21.9 ± 2.0 |
| | 7000 kDa | 21.5 ± 0.5 |
| | ESGA(24000 kDa) | 16.9 ± 2.4 |
| | ESGB(5000 kDa) | 16.9 ± 2.0 |
| | 14000 kDa | 17.9 ± 1.8 |
| Natural | Oyster (Wako Pure Chemical Industries) | ND |
| | Sweet Corn (Kewpie) | ND |
| | Biosaccharide (Yamakawa & Co., Ltd. (mussel) "NG") | ND |
| | Bovine Liver (Sigma) | ND |

Not Detected: <0.2%

The above-described results have revealed that the natural glycogens are substantially digested by pancreatin and glucoamylase, while the enzymatically synthesized glycogens have a resistant starch (RS) content of about 20%. The resistant starch is particularly preferable as the glycogen of the invention having various pharmacological effects.

Method 2

Fifty milligrams of a sample are reacted with α-amylase (product of Sigma, Type I-A isolated from porcine pancreas, enzyme amount: 300 U/g substrate) in 1 mL of a reaction solution. The pH of the reaction solution is adjusted to 7 with 10 mM phosphate buffer.

↓ 37° C., 0.5, 1, 3, 6, or 24 hr

The reaction is stopped by heating for 5 minutes at 100° C., the reaction solution is filtered with a 0.45 μm filter, and the filtrate is analyzed by HPLC under the following conditions. Specifically, Shodex OH-Pack SB806MHQ (Showa Denko; inside diameter: 8 mm, length: 300 mm) was used as a column, Shodex OH-Pack SB-G (Showa Denko; inside diameter: 6 mm, length: 50 mm) was used as a guard column, and a multi-angle light scattering detector (DAWN-DSP or DAWN-Heleos; Wyatt Technology) and a differential refractometer (Shodex RI-71 or RI-101; Showa Denko) were used as detectors by connecting them in sequence. The column was maintained at 40° C., and 0.1 M sodium nitrate solution was used as an eluate at a flow rate of 1 mL/min. The signal obtained from the peak of α-glucan, which is eluted in about 6 to 11 minutes, is collected using data analysis software (trade name: ASTRA; Wyatt Technology), and the weight average molecular weight (Mw) is determined through analysis using the software. The ratio between the weight average molecular weights (Mw) before and after the α-amylase treatment is determined by this method. The results are shown in FIG. 4.

Figure 4:
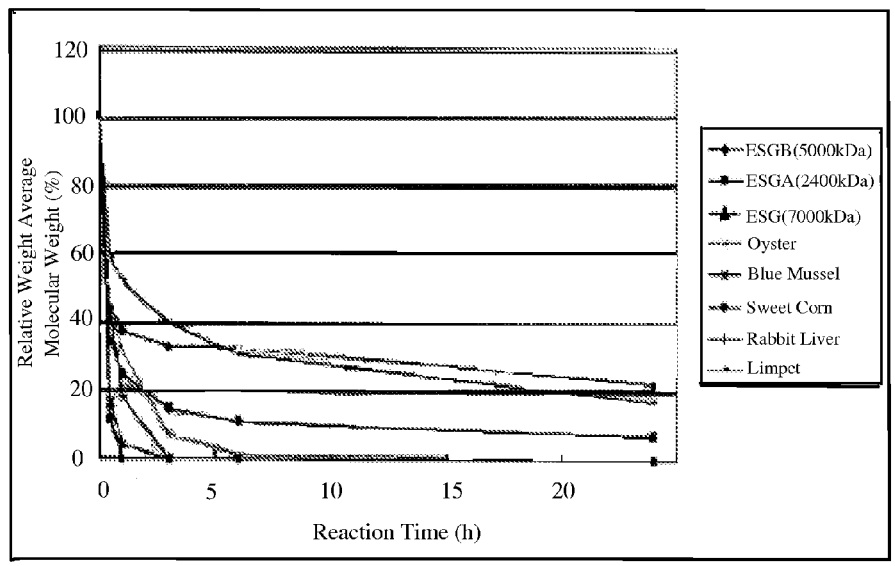
FIG. 4 is a graph showing the results for the digestion of glycogen derived from various materials by α-amylase.

As shown in the results of FIG. 4, the natural glycogens such as those from mussel and sweet corn were rapidly digested, while the synthetic glycogens (ESGA, ESGB, ESG (7000 kDa)) retained 5 to 40% of their molecular weight before digestion, and hence proved to be preferred as starting materials. The results have also revealed that among natural glycogens, glycogen derived from oyster is relatively resistant to the α-amylase digestion, and glycogen derived from limpet is particularly resistant and preferable.

Test Example 2

Figure 5:
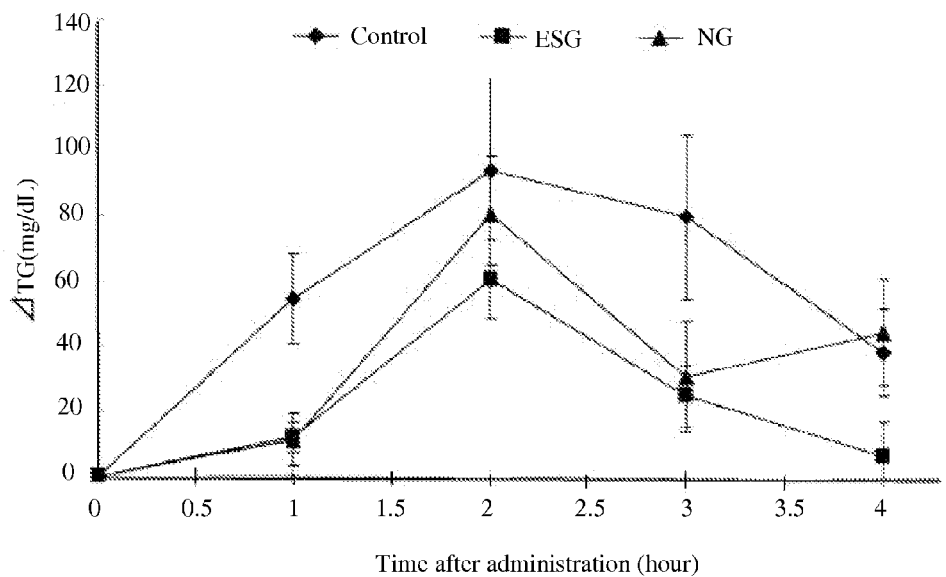
FIG. 5 is a graph showing the inhibitory effect of glycogen on the absorption of neutral fats.

Inhibitory Effects on the Absorption of Fat and the Accumulation of Fat in the Liver 1. Single Lipid Dose Test SD rats (7-9 weeks old, male) fasted for 18 hours were orally administered water (control) or 20% ESG solution or 20% NG (Natural Glycogen) solution in a dose of 10 ml/kg body weight. Immediately after this, a corn oil emulsion (corn oil: 20%, lecithin: 1.2%, glycerin: 2.3%) was orally administered in a dose of 10 ml/kg body weight. Blood was collected via the tail vein before and 1, 2, 3, and 4 hours after the administration, after which the blood plasma was separated by centrifugation, and the concentration of triacylglycerol in the plasma was measured using a WAKO kit. The results are shown in FIG. 5.

2. High Fat Diet Test

Figure 6:
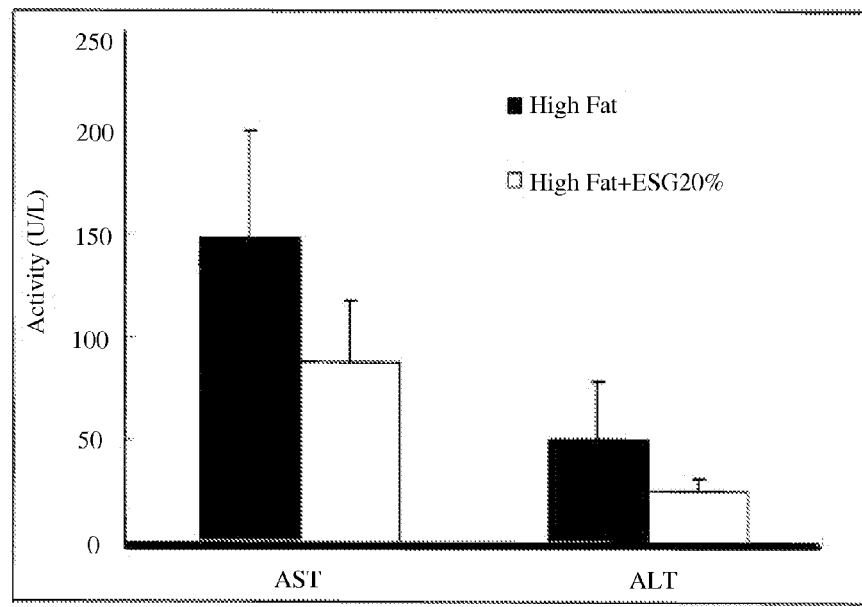
FIG. 6 is a bar chart showing the effect of glycogen on AST and ALT.
Figure 7:
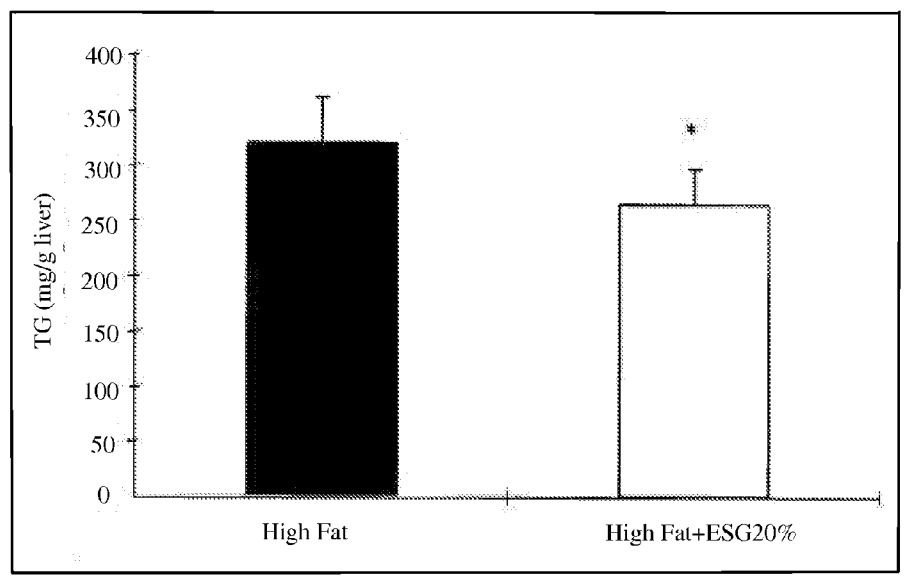
FIG. 7 is a bar chart showing the effect of glycogen on the accumulation of liver fat.

SD rats (7 weeks old, male) were divided into two groups of eight rats per group, one group being a high fat diet group, and the other being a high fat diet+ESG20% group. Each group was allowed to freely ingest feed having the composition shown in the following table for 4 weeks. After the completion of feeding, various fat tissues were excised and weighed. Further, blood plasma and livers were collected, and aspartate aminotransferase (AST) and alanine aminotransferase (ALT) activities were measured using a commercially available kit (product of Wako). The neutral fats in the liver were measured by extracting the total lipids according to the Folch method, dissolving the lipids in isopropanol, and quantifying the lipids with a commercially available kit (product of Wako). Note that the asterisk * indicates a significant difference over the high fat diet group (P<0.05, t-test). The results are shown in FIGS. 6 and 7, and Table 10.

TABLE 10

Diet Compositions Used in the High Fat Diet Test

| | High Fat | High Fat + ESG20% |
|---|---|---|
| Corn Starch | 35.57% | 21.64% |
| Milk Casein | 14.00% | 14.00% |
| Pregelatinized Corn Starch | 15.50% | 9.43% |
| Granulated Sugar | 10.00% | 10.00% |
| Refined Soybean Oil | 4.00% | 4.00% |
| Avicel (Cellulose Powder) | 5.00% | 5.00% |
| Mineral Mix (AIN-93M-MX) | 3.50% | 3.50% |
| Vitamin Mix (AIN-93VX) | 1.00% | 1.00% |
| L-Cystine | 0.18% | 0.18% |
| Choline Bitartrate | 0.25% | 0.25% |
| Tert-Butylhydroquinone | 0.0030% | 0.0030% |
| Cholesterol | 1.00% | 1.00% |
| Coconut Oil | 10.00% | 10.00% |
| GL | 0.00% | 20.000% |

TABLE 11

Effects of ESG on Body Fat Mass

| | Group | |
|---|---|---|
| | High Fat | High Fat + ESG20% |
| Fat Tissue | (% Body Weight) | |
| Fat around the Kidney | 2.81 ± 0.33 | 2.08 ± 0.23* |
| Subcutaneous Fat | 3.08 ± 0.67 | 2.03 ± 0.28* |
| Fat around the Testis | 2.23 ± 0.42 | 1.76 ± 0.32* |

As is clear from the results of Table 11 and FIGS. 5 to 7, glycogen proved to inhibit the accumulation of fat in the liver, subcutaneous tissue, and areas around the kidney and testis, as well as inhibiting visceral fat and its absorption.

The invention claimed is:

1. A method for suppressing a blood glucose level increase and an insulin secretion amount per unit calorie intake in a subject in need thereof, comprising orally administering enzymatically synthesized glycogen (ESG) to the subject.

2. A method for reducing a proportion of body fat relative to body weight of a subject in need thereof, comprising orally administering enzymatically synthesized glycogen (ESG) to the subject.

3. The method of claim 2, wherein the body fat is visceral fat.

4. A method for suppressing a body weight increase in a subject in need thereof, comprising orally administering enzymatically synthesized glycogen (ESG) to the subject.

5. A method for regulating gastrointestinal conditions in a subject in need thereof, comprising orally administering enzymatically synthesized glycogen (ESG) to the subject.

6. A method for promoting *Bifidobacterium* growth in a subject in need thereof, comprising orally administering enzymatically synthesized glycogen (ESG) to the subject.

7. A method for increasing a proportion of *Bifidobacteria* among enteric bacteria in a subject in need thereof, comprising orally administering enzymatically synthesized glycogen (ESG) to the subject.

8. A method for promoting *Lactobacillus* growth in a subject in need thereof, comprising orally administering enzymatically synthesized glycogen (ESG) to the subject.

9. A method for increasing a proportion of *Lactobacillus* among enteric bacteria in a subject in need thereof, comprising orally administering enzymatically synthesized glycogen (ESG) to the subject.

10. A method for reducing a blood neutral fat level in a subject in need thereof, comprising orally administering enzymatically synthesized glycogen (ESG) to the subject.

11. A method for reducing a total blood cholesterol level in a subject in need thereof, comprising orally administering enzymatically synthesized glycogen (ESG) to the subject.

12. A method for increasing a proportion of HDL cholesterol relative to a total blood cholesterol in a subject in need thereof, comprising orally administering enzymatically synthesized glycogen (ESG) to the subject.

* * * * *